(12) United States Patent
Schlueter et al.

(10) Patent No.: US 7,832,405 B1
(45) Date of Patent: Nov. 16, 2010

(54) METHOD AND APPARATUS FOR ASSEMBLING IMPLANTS

(75) Inventors: Trevor S Schlueter, Leesburg, IN (US); Robert Metzger, Wakarusa, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 1440 days.

(21) Appl. No.: 10/925,628

(22) Filed: Aug. 25, 2004

(51) Int. Cl.
*A61F 1/04* (2006.01)

(52) U.S. Cl. ...................................... 128/898

(58) Field of Classification Search ..... 623/13.12–13.2, 623/20.14–20.36; 606/79–81, 86–88
See application file for complete search history.

(56) References Cited

U.S. PATENT DOCUMENTS

| | | | | |
|---|---|---|---|---|
| 4,459,985 A | * | 7/1984 | McKay et al. | 606/100 |
| 4,467,801 A | * | 8/1984 | Whiteside | 606/88 |
| 4,549,319 A | * | 10/1985 | Meyer | 623/23.23 |
| 4,773,407 A | * | 9/1988 | Petersen | 606/88 |
| 4,919,679 A | * | 4/1990 | Averill et al. | 623/22.12 |
| 4,921,493 A | * | 5/1990 | Webb et al. | 606/85 |
| 4,936,853 A | * | 6/1990 | Fabian et al. | 623/20.15 |
| 4,993,410 A | * | 2/1991 | Kimsey | 606/100 |
| 5,061,271 A | * | 10/1991 | Van Zile | 623/23.35 |
| 5,108,402 A | * | 4/1992 | Chin | 606/93 |
| 5,180,384 A | * | 1/1993 | Mikhail | 606/80 |
| 5,181,925 A | * | 1/1993 | Houston et al. | 623/20.15 |
| 5,275,603 A | * | 1/1994 | Ferrante et al. | 606/86 |
| 5,356,414 A | * | 10/1994 | Cohen et al. | 606/88 |
| D353,001 S | * | 11/1994 | Petersen | D24/142 |
| 5,409,492 A | * | 4/1995 | Jones et al. | 606/86 |
| 5,443,471 A | * | 8/1995 | Swajger | 606/99 |
| 5,476,466 A | * | 12/1995 | Barrette et al. | 606/86 |
| 5,609,642 A | * | 3/1997 | Johnson et al. | 606/88 |
| 5,683,469 A | * | 11/1997 | Johnson et al. | 623/20.32 |
| 5,690,636 A | * | 11/1997 | Wildgoose et al. | 606/88 |
| 5,776,200 A | * | 7/1998 | Johnson et al. | 623/20.15 |
| 5,788,701 A | * | 8/1998 | McCue | 606/88 |
| 5,976,147 A | * | 11/1999 | LaSalle et al. | 606/88 |
| 6,159,216 A | * | 12/2000 | Burkinshaw et al. | 606/88 |
| 6,238,435 B1 | * | 5/2001 | Meulink et al. | 623/22.12 |
| 6,355,045 B1 | * | 3/2002 | Gundlapalli et al. | 606/88 |
| 6,355,069 B1 | * | 3/2002 | DeCarlo et al. | 623/23.26 |
| 6,520,966 B1 | * | 2/2003 | Kohler et al. | 606/86 |
| 6,589,283 B1 | * | 7/2003 | Metzger et al. | 623/20.35 |
| 6,626,913 B1 | * | 9/2003 | McKinnon et al. | 606/99 |
| 6,656,188 B2 | * | 12/2003 | Naybour et al. | 606/86 |
| 6,764,492 B2 | * | 7/2004 | Taft | 606/86 |
| 2003/0078669 A1 | * | 4/2003 | Martin et al. | 623/20.32 |
| 2004/0073315 A1 | * | 4/2004 | Justin et al. | 623/20.15 |
| 2005/0075638 A1 | * | 4/2005 | Collazo | 606/80 |

\* cited by examiner

*Primary Examiner*—David Isabella
*Assistant Examiner*—Ann Schillinger
(74) *Attorney, Agent, or Firm*—Harness, Dickey

(57) ABSTRACT

An apparatus and method for implanting a prosthesis includes implanting a first component into a recess in a bone. The first component defines a main body defining a receiving portion and a locating bore. A second component is located into engagement with the first component, the second component defining a passage therethrough. A rod is inserted through the passage defined on the second component and into the locating bore of the first component. A handle associated with the rod is slidably actuated into contact with the second component to matingly lock the first component to the second component.

21 Claims, 3 Drawing Sheets

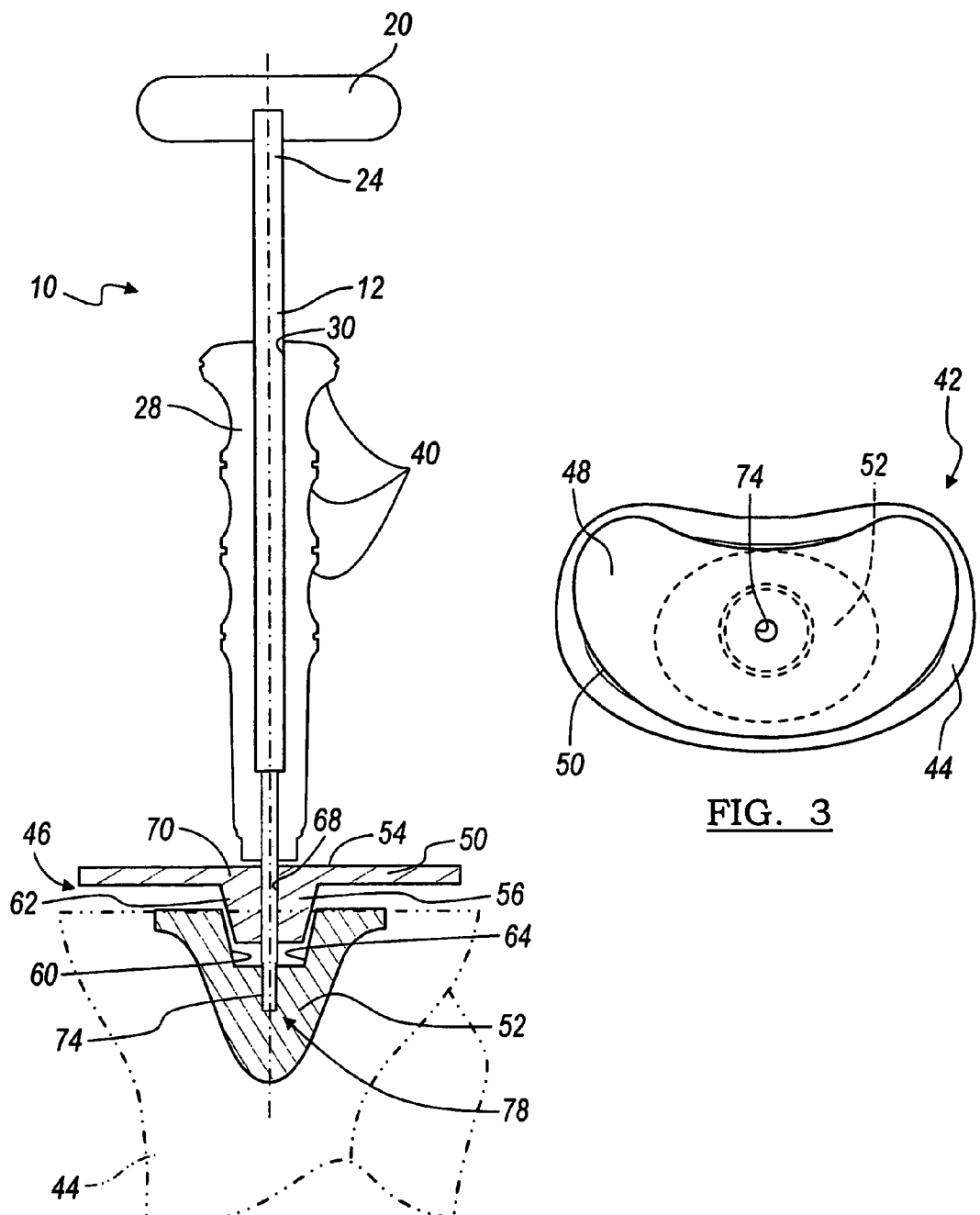

METHOD AND APPARATUS FOR ASSEMBLING IMPLANTS

FIELD OF THE INVENTION

The present invention relates to assembling implants and more particularly to in-vivo assembly of a tibial tray.

BACKGROUND OF THE INVENTION

A knee joint prosthesis typically comprises a femoral component and a tibial component. The femoral component and the tibial component are designed to be surgically attached to the distal end of the femur and the proximal end of the tibia, respectively. The femoral component is further designed to cooperate with the tibial component in simulating an articulating motion of an anatomical knee joint.

In one application, a tibial component includes a modular tibial tray connected to a modular tibial stem and implanted at the proximal tibia. Typically during a tibial preparation procedure, portions of the proximal tibia may be resected to define a surface for accepting the tibial tray. In addition, a recess may be prepared in the tibial bone to accept the tibial stem. Typically, the tibial stem is assembled to the tibial tray ex-vivo prior to implanting onto the proximal tibia. In one example, a mallet is used to couple the tray to the stem.

In some instances it is inconvenient to couple implants such as the tibial tray to the tibial stem ex-vivo prior to implanting with a given bone such as on a proximal tibia. What is needed is a system for providing convenient and robust in-vivo assembly of implants.

SUMMARY OF THE INVENTION

An apparatus and method for implanting a prosthesis includes implanting a first component into a recess in a bone. The first component defines a main body defining a receiving portion and a locating bore. A second component is located into engagement with the first component, the second component defining a passage therethrough. A rod is inserted through the passage defined on the second component and into the locating bore of the first component. A handle associated with the rod is slidably actuated into contact with the second component to matingly lock the first component to the second component.

According to other features, the receiving portion of the first component defines tapered sidewalls. The insertion portion defines tapered sidewalls for mating with the tapered sidewalls of the receiving portion. The locating bore of the first component is centrally positioned on the main body portion and substantially parallel to a longitudinal axis of the bone. The distal end of the rod is threaded for threadably mating with the locating bore. The rod includes a stopping member arranged on a proximal end. The handle is bound between the stopping member and the second component during slidable actuation.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 2 is a sectional view of the slaphammer of FIG. 1 shown implanting a tibial tray with a tibial stem into a proximal end of a tibia;

FIG. 3 is a plan view of the tibial tray of FIG. 2;

DETAILED DESCRIPTION OF THE PREFERRED EMBODIMENTS

The following description of the preferred embodiment(s) is merely exemplary in nature and is in no way intended to limit the invention, its application, or uses. For example, while the following discussion is specifically directed toward implanting a tibial tray with respect to a tibial stem onto a proximal tibia, it is appreciated that the present teachings are not so limited. In this way, the present teachings may be similarly directed toward in-vivo assembly of other implants where relative coupling between two components of any type of implant assembly is needed.

Figure 1:
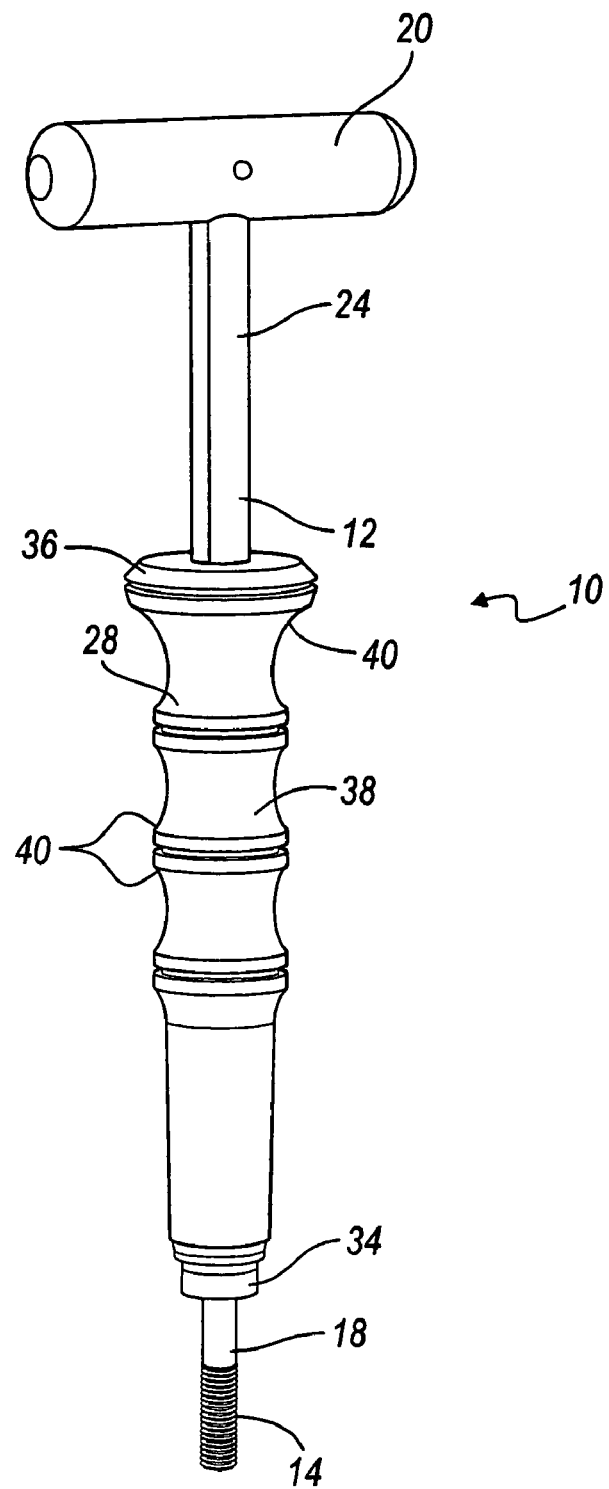
FIG. 1 is a perspective view of a slaphammer according to the present teachings.

With initial reference to FIG. 1, a slaphammer for in-vivo assembly of implants according to the present teachings is shown and generally identified at reference 10. The slaphammer 10 generally includes a rod 12 having a threaded portion 14 arranged on a distal end 18 and a stopping member 20 arranged on a proximal end 24. A handle 28 is adapted for slidable communication along the rod 12. As will be explained more fully in the discussion below, the slaphammer 10 is operable to facilitate in-vivo assembly of implants, such as complementary implants.

With continued reference to FIG. 1 and further reference to FIG. 2, the slaphammer 10 will be described in greater detail. It is appreciated that while the rod 12 is shown to have a rectangular cross section on the proximal end 24 and a circular cross section on the distal end 18, the cross sections are merely exemplary. An inner passage 30 is defined axially through the handle 28 of the slaphammer 10 for slidably accepting the rod 12 therethrough. The handle 28 includes a distal end portion 34, a proximal end portion 36 and an intermediate portion 38. The distal end portion 34 is adapted to impart a blow onto the surface of an implant as will be described. The proximal end portion 36 of the handle 28 is bound by the stopping member 20 during slidable actuation along the rod 12. The intermediate portion 38 includes a series of ergonomic groove portions 40 formed radially around an outer surface for providing a favorable gripping surface.

With continued reference to FIG. 1 and further reference to FIGS. 2 and 3, the slaphammer 10 is shown operatively associated with a knee joint prosthesis 42. Again, the slaphammer 10 can be used to assemble any type of implant having multiple components that required attachment to one another using any type of attachment mechanism, such as for example a Morse taper connection. The knee joint prosthesis 42 is shown being secured to a tibia 44 of a surgically resected left knee joint, with the tibia 44 shown in phantom, and with the understanding that a suitable right knee joint prosthesis can be similarly constructed. The knee joint prosthesis 42 generally may include a tibial component 46 having a floating tibial bearing 48. While not specifically shown, the tibial bearing 48 may be located between the tibial component 46 and a femoral component secured to a distal end of a femur.

The tibial component 46 is adapted to be secured to the proximal end of the tibia 44 after the tibia 44 has been resected in a manner known in the art. The tibial component 46 includes a substantially planar platform-like tibial tray 50 and an inferiorly extending tibial stem 52. The tibial tray 50 includes an upper bearing surface 54. The tibial stem 52 is adapted to be received in a corresponding opening made by the surgeon in the intramedullary canal of the tibia 44. The tibial tray 50 defines a male extension portion 56 for being accepted into a complementary female receiving portion 60 according to the present teachings as will be described in greater detail herein. The male extension portion 56 includes a conically tapered sidewall 62. The female receiving portion 60 defines a conically tapered bore 64. The conically tapered sidewall 62 is operable to be nestingly received within the conically tapered bore 64 to provide a friction fit that forms a Morse-type taper. It is appreciated that the respective male extension portion 56 and female receiving portion 60 may be reversed.

A central passage 68 is defined through a central body portion 70 of the tibial tray 50 for passing the rod therethrough during assembly of the tibial tray 50 onto the tibial stem 52. A locating bore 74 having threads is defined inferiorly of the stem 52 at a terminal surface of the female receiving portion 60 for accepting the distal end 18 of the rod 12. The tibial tray 50 and tibial stem 52 are preferably manufactured from cobalt-chromium-molybdenum or any other suitable biocompatible material. The top of the tibial tray 50 provides a substantially smooth tibial bearing surface.

Figure 4:
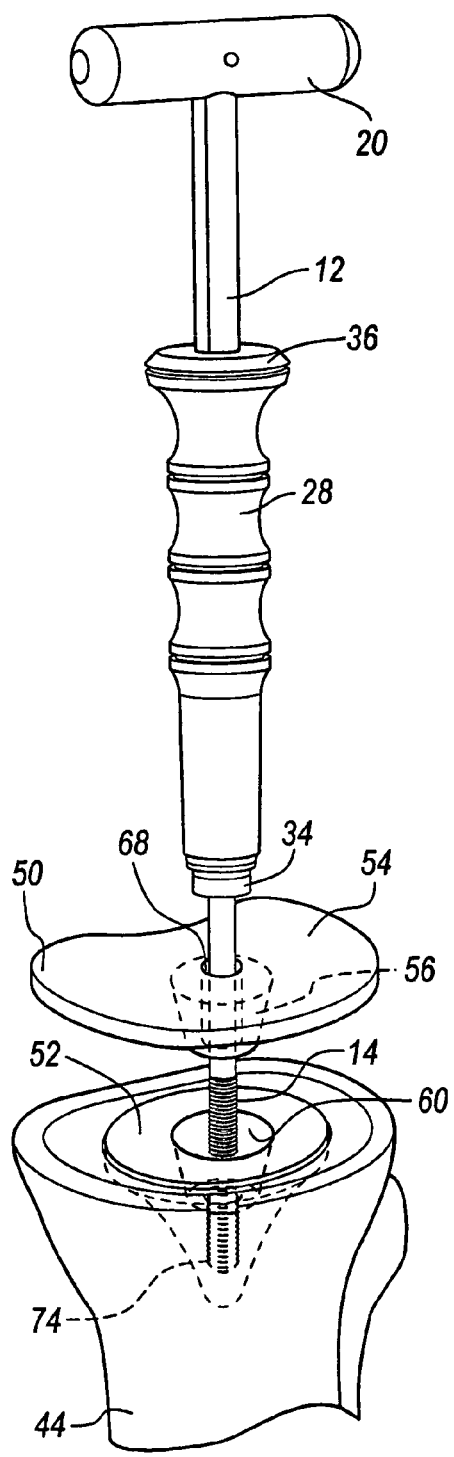
FIG. 4 is an exploded assembly view of the slaphammer and tibial tray shown prior to engagement with the tibial stem.
Figure 5:
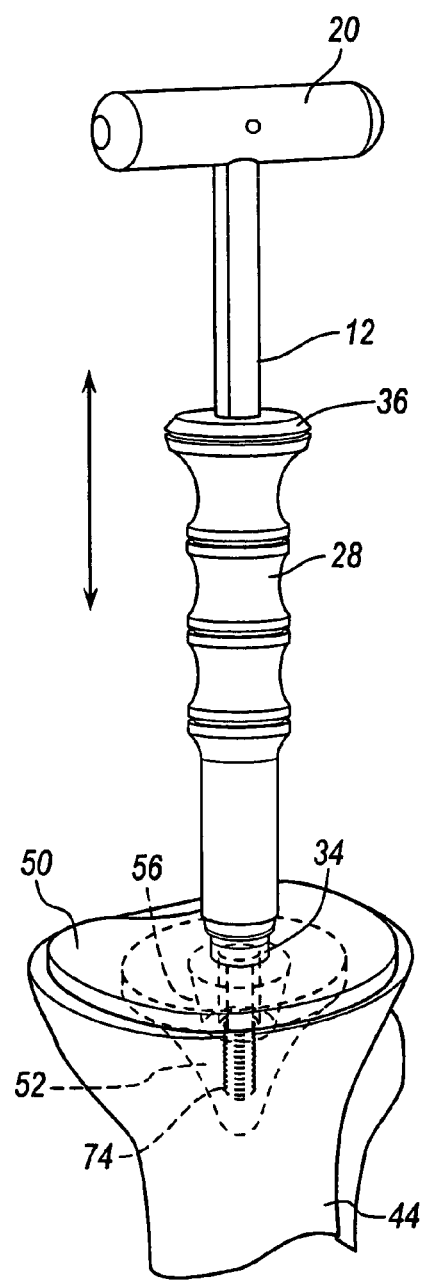
FIG. 5 is a perspective view of the slaphammer shown with the tibial tray received by the tibial stem after sufficient actuation of the slaphammer during assembly.

With further reference now to FIGS. 4 and 5, assembly of the tibial stem 52 and tibial tray 50 onto a proximal end of the tibia 44 will be described. Initially, the tibial stem 52 is placed into the opening made by the surgeon in the center of the tibia 44. It is appreciated that the upper surface of the tibial stem 52 may be left proud with respect to the proximal surface of the tibia 44 or alternatively be flush with the proximal surface of the tibia 44. Next, the tibial tray 50 is set onto the tibial stem 52. In this regard, the male extension portion 56 is aligned axially with the female receiving portion 60 and advanced downwardly (as viewed from FIG. 4) until the respective conically tapered sidewalls 62 and 64 engage.

At this point, the distal end 18 of the rod 12 is passed through the passage 68 of the tibial tray 50 and engaged with the locating bore 74. It is appreciated that the distal end 18 of the rod 12 may be initially passed through the passage 68 of the tibial tray 50 subsequent to locating the tibial tray 50 onto the tibial stem. The locating bore 74 acts to orient the rod 12 in a generally transverse relationship with the tibial tray 50. In the exemplary illustrations provided, a threadable interface 78 is provided between the distal end 18 of the rod 12 and the locating bore 74. As a result, the transversely extending stopping member 20 may be grasped and rotated about an axis of the rod 12 to impart sufficient torque at the threaded interface 78. It is appreciated that while threads 14 are shown associated with the distal end 18 of the rod 12 and incorporated on the locating bore 74 for achieving an engaged relationship between the rod 12 and the locating bore 74, other mechanical configurations may be employed, such as for example spring loaded locking tabs, magnetic interface or any other suitable coupling interface. Alternatively, the distal end 18 of the rod 12 and the locating bore 74 may each present a smooth surface without providing any relative coupling action.

Next, the male extension portion 56 of the tibial tray 50 is driven into engagement with the female receiving portion 60 of the tibial stem 52 by slidable actuation of the handle 28. Explained further, while holding the stopping member 20, the handle 28 is driven linearly along the rod 12 such that the distal end portion 34 impacts the upper bearing surface 54 of the tibial tray 50. The impacting force causes the tibial tray 50 to slidably engage with the stem 52 along respective tapered sidewalls 62 and 64. In some instances a single blow with the handle 28 may cause the male extension portion 56 to sufficiently nest within the female receiving portion 60 such that the tibial tray 50 is flush with the proximal tibia (FIG. 5). In other instances, it may be necessary to strike one or more subsequent blows onto the tibial tray 50 with the handle 28. As such, the handle 28 is advanced along the rod 12 in a direction away from the tibial tray 50. The handle 28 may be advanced into engagement with the stopping member 20 or to a position along the rod 12 a distance from the tibial tray 50. The handle 28 is then driven into impact with the tibial tray 50 as previously described. These steps are repeated as necessary until the tibial tray 50 achieves a desired relationship with the tibial stem (FIG. 5). Finally, the rod 12 is retracted from the locating bore 74. This step may include threadably retracting the rod 12 from the threads of the locating bore 74, or disengaging a coupling interface employed at the distal end 18 of the rod 12 and the locating bore 74. It is appreciated that in some instances, the slaphammer 10 may be removed once the respective tapered sidewalls 62 and 64 achieve partial engagement. Subsequent to removal of the slaphammer 10, the tibial tray 50 may be further seated onto the proximal tibia such as by a mallet or other impacting instrument.

Those skilled in the art can now appreciate from the foregoing description that the broad teachings of the present invention can be implemented in a variety of forms. For example while the description herein relates to implanting a tibial tray, the slaphammer may be used for implanting associated with a femur, a hip, and a shoulder for example. In this way, the slaphammer may be used to facilitate in-vivo assembly at the implant site whereby a first component is located at the implant site and a second component is introduced and subsequently coupled to the first component. Therefore, while this invention has been described in connection with particular examples thereof, the true scope of the invention should not be so limited since other modifications will become apparent to the skilled practitioner upon a study of the drawings, the specification and the following claims.

What is claimed is:

1. A method of implanting a knee prosthesis comprising:
   implanting a first component into a recess in a bone to a position flush with a proximal end of said bone, said first component defining a main body defining a receiving portion and a locating bore;
   locating a second component into engagement with said first component, said second component defining a first end and a second end and a passage that extends entirely through the second component from the first end to the second end;
   inserting a rod completely through said passage defined on said second component and into said locating bore of said first component; and
   slidably actuating a handle associated with said rod along said rod and into contact with said second component to matingly lock said first component to said second component.

2. The method of claim 1, further comprising removing said rod from said locating bore.

3. The method of claim 2 wherein removing said rod includes rotating a proximal end portion of said rod thereby retracting a threaded portion of said rod from complementary threads formed on said locating bore.

4. The method of claim 1 wherein locating said second component includes inserting a male extension portion into said receiving portion of said first component.

5. The method of claim 4 wherein inserting said male extension portion includes locating tapered sidewalls of said male extension portion into engagement with tapered sidewalls of said receiving portion.

6. The method of claim 5 wherein repeated actuation of said handle progressively advances said male extension portion into said receiving portion until an underside surface of said second component locates with an upper surface of said first component.

7. The method of claim 1 wherein inserting said rod includes threadably engaging a distal end of said rod with complementary threads formed on said locating bore.

8. The method of claim 1 wherein slidably actuating a handle into contact with said second component includes impacting a first end of said handle with an upper face of said second component.

9. The method of claim 1 wherein slidably actuating said handle into contact with said second component includes impacting an uppermost face of said second component.

10. A method of implanting a knee prosthesis comprising:
   implanting a first component into a recess in a bone, said first component defining a main body defining a conically tapered receiving portion;
   locating a second component into engagement with said first component, said second component defining an opening and a conically tapered extension portion;
   inserting a rod completely through said opening defined on said second component;
   slidably actuating a handle associated with said rod along said rod and into contact with said second component to matingly lock said conically tapered extension portion with said conically tapered receiving portion; and
   repeatedly impacting a first end of said handle with an upper face of said second component to progressively advance said conically tapered extension portion into said conically tapered receiving portion.

11. The method of claim 10 wherein inserting said rod comprises inserting said rod through said opening defined on said second component and into a locating bore defined on said first component.

12. The method of claim 11 wherein inserting said rod includes threadably engaging a distal end of said rod with complementary threads formed on said locating bore.

13. The method of claim 12, further comprising removing said rod from said locating bore wherein removing said rod includes rotating a proximal end portion of said rod thereby retracting a threaded portion of said rod from said complementary threads formed on said locating bore.

14. The method of claim 10 wherein repeatedly impacting said handle creates a Morse-type taper fit between said conically tapered extension portion and said conically tapered receiving portion.

15. The method of claim 10 wherein implanting said first component includes locating said first component at a location in contact with a proximal end of said bone and slidably actuating said handle into contact with said second component includes impacting an uppermost face of said second component.

16. A method of implanting a prosthesis comprising:
   inserting a stem into a recess on a proximal end of a tibia to a position flush with said proximal end of said tibia, said stem having a main body portion defining a tapered receiving bore;
   inserting a tapered extension portion of a tibial tray into said tapered receiving bore of said stem;
   passing a rod through a passage defined through said tibial tray and into engagement with said stem;
   slidably actuating a handle communicating with said rod into contact with said tibial tray, whereby actuation of said handle encourages said tapered extension portion of said tibial tray to be matingly received by said tapered receiving bore; and
   repeatedly impacting a first end of said handle with an upper face of said tibial tray to progressively advance said tapered extension portion into said tapered receiving portion.

17. The method of claim 16 wherein passing said rod comprises passing said rod through said passage defined on said tibial tray and into a locating bore defined on said stem.

18. The method of claim 17 wherein passing said rod includes threadably engaging a distal end of said rod with complementary threads formed on said locating bore.

19. The method of claim 18, further comprising removing said rod from said locating bore, wherein removing said rod includes rotating a proximal end portion of said rod thereby retracting a threaded portion of said rod from said complementary threads formed on said locating bore.

20. The method of claim 16 wherein slidably actuating said handle comprises:
   translating a handle along a longitudinal shaft between a stopping member disposed at a proximal end of said shaft and said tibial tray, wherein said handle portion creates a Morse-type taper fit between said tapered extension portion and said tapered receiving portion.

21. The method of claim 16 wherein slidably actuating said handle into contact with said tibial tray includes impacting an uppermost face of said second component.

* * * * *